(12) United States Patent
Faergemann et al.

(10) Patent No.: US 9,757,596 B2
(45) Date of Patent: Sep. 12, 2017

(54) COMPOSITION COMPRISING AT LEAST 3 DIFFERENT DIOLS

(75) Inventors: Jan Faergemann, Göteborg (SE); Thomas Hedner, Gällstad (SE)

(73) Assignee: AMBRIA DERMATOLOGY AB, Helsingborg (SE)

( * ) Notice: Subject to any disclaimer, the term of this patent is extended or adjusted under 35 U.S.C. 154(b) by 1722 days.

(21) Appl. No.: 11/791,577

(22) PCT Filed: Nov. 29, 2005

(86) PCT No.: PCT/SE2005/001787
§ 371 (c)(1),
(2), (4) Date: Mar. 25, 2008

(87) PCT Pub. No.: WO2006/057616
PCT Pub. Date: Jun. 1, 2006

(65) Prior Publication Data
US 2009/0221716 A1    Sep. 3, 2009

Related U.S. Application Data

(60) Provisional application No. 60/631,148, filed on Nov. 29, 2004.

(30) Foreign Application Priority Data

Nov. 29, 2004    (SE) ..................... 0402890

(51) Int. Cl.
| | | |
|---|---|---|
| A01N 31/00 | (2006.01) |
| A61K 31/045 | (2006.01) |
| A61Q 17/00 | (2006.01) |
| A01N 31/02 | (2006.01) |
| A61K 8/34 | (2006.01) |
| A61K 31/047 | (2006.01) |
| A61Q 19/00 | (2006.01) |

(52) U.S. Cl.
CPC ........... *A61Q 17/005* (2013.01); *A01N 31/02* (2013.01); *A61K 8/345* (2013.01); *A61K 31/047* (2013.01); *A61Q 19/00* (2013.01); *A61K 2800/524* (2013.01); *A61K 2800/59* (2013.01)

(58) Field of Classification Search
CPC .... A01N 31/02; A01N 2300/00; A61K 8/345; A61K 31/047; A61K 2800/59; A61K 2800/524
USPC ........................................................ 514/738
See application file for complete search history.

(56) References Cited

U.S. PATENT DOCUMENTS

| | | | |
|---|---|---|---|
| 3,836,672 A | 9/1974 | Wright | |
| 4,507,287 A * | 3/1985 | Dixon ................ | A61K 9/0014 514/43 |
| 4,552,872 A | 11/1985 | Cooper et al. | |
| 4,855,294 A | 8/1989 | Patel et al. | |
| 5,026,556 A | 6/1991 | Drust et al. | |
| 5,041,439 A | 8/1991 | Kasting et al. | |
| 5,814,305 A * | 9/1998 | Laugier ................ | A61K 8/33 424/61 |
| 6,123,953 A | 9/2000 | Greff | |
| 2002/0098211 A1 | 7/2002 | Cupferman et al. | |
| 2002/0160023 A1* | 10/2002 | Bagdi et al. .................. 424/401 | |
| 2004/0010222 A1* | 1/2004 | Nunomura et al. ............ 604/22 | |
| 2004/0047826 A1* | 3/2004 | Brown ....................... 424/70.12 | |
| 2004/0248993 A1* | 12/2004 | Faergemann et al. ........ 514/738 | |
| 2005/0058679 A1 | 3/2005 | Kropke et al. | |

FOREIGN PATENT DOCUMENTS

| | | |
|---|---|---|
| DE | 2 204 943 | 8/1973 |
| EP | 0 249 397 | 12/1987 |
| EP | 0 351 897 | 1/1990 |
| GB | 1 604 856 | 12/1981 |
| JP | 48-28652 | 4/1973 |
| WO | WO 90/15597 | 12/1990 |
| WO | WO 96/11572 | 4/1996 |
| WO | WO 00/72883 A2 | 12/2000 |
| WO | WO 01/00139 A1 | 1/2001 |
| WO | WO 03/066012 | 8/2003 |
| WO | WO 03/069994 | 8/2003 |
| WO | WO 03/069994 A1 | 8/2003 |
| WO | WO 2004/112765 | 12/2004 |

OTHER PUBLICATIONS

STN search Report 1—2011, p. 1-7.*
STN search Report 2—2011, p. 1-7.*
Faergemann (Current Therapeutic Research, 43, 3, 1988).*
Faergemann (Sabouraudia, 1980, 287-293).*
European Search Report from EP Application No. 05804731.7 mailed Apr. 6, 2011.

* cited by examiner

*Primary Examiner* — Uma Ramachandran
(74) *Attorney, Agent, or Firm* — Merchant & Gould P.C.

(57) ABSTRACT

The present invention relates to a composition comprising at least 3 different diols, wherein said diols have the general structure $(CH_2)_nH_2O_2$, wherein n is the number of $CH_2$ and being between 3 to 10, in a total amount of from about 0.1 to about 50% (v/v), a method for producing the composition and its use, such as in therapy. The composition may be a pharmaceutical, cosmetic, antimicrobial or preservative composition. The composition is useful in inactivating microorganisms or preventing their growth.

14 Claims, No Drawings

COMPOSITION COMPRISING AT LEAST 3 DIFFERENT DIOLS

FIELD OF THE INVENTION

The present invention relates to a composition comprising at least 3 different diols, wherein said diols have the general structure $(CH_2)_n H_2 O_2$, wherein n is the number of $CH_2$ and being between 3 to 10, in a total amount of from about 0.1 to about 50% (v/v), a method for producing the composition and its use, such as in therapy. The composition may be a pharmaceutical, cosmetic, antimicrobial or preservative composition. The composition is useful in inactivating microorganisms or preventing their growth.

BACKGROUND OF THE INVENTION

Microbes may be inactivated in different ways depending on the purpose for inactivating them. The approach differs depending on whether the purpose is to prevent growth of microorganisms, to inhibit further growth or to reduce and eliminate the microorganism. Additionally the approach differs depending on where the microorganism is located such as in a liquid, on a surface, within a mammalian body etc. However, there are certain conditions which need to be fulfilled which are independent of the criteria mentioned above. In addition to being highly effective, the composition to be used should be non-toxic, non-allergenic, environmentally friendly and possible to manufacture at reasonable cost.

One example of such an agent is propane-1,2-diol (propylene glycol), which is the only diol widely used to inactivate microorganisms in dermatology. In addition, pentane-1,5-diol has been used as a component in topical pharmaceutical compositions, where it has been shown to increase the percutaneous absorption of active substances more efficiently than propane-1,2-diol. The water binding capacity of pentane-1,5-diol is largely comparable to that of propane-1,2-diol, but it penetrates more efficiently into the deepest parts of stratum corneum of the skin. In addition, pentane-1,5-diol is cosmetically attractive, presents a low risk for skin and eye irritation compared to other diols, has low toxicity and is odourless.

WO 03/035021 discloses a topical composition for skin care or administration of a pharmacologically active agent in form of a lotion, cream or similar that comprises from 5% to 70% by weight of pentane-1,5-diol in a cosmetically or pharmaceutically acceptable carrier.

Multi-resistance of bacteria to antibiotics is becoming more and more common. In the health sector there is today a mounting concern worldwide regarding the future use of traditional antimicrobials. Alternative methods and approaches have to be used to manufacture affective antimicrobial agents. PCT/SE2004/001001 discloses the in-vitro effect of pentane-1,5-diol against both antibiotic sensitive and multi-resistant gram-positive and gram-negative bacteria. Pentane-1,5-diol was highly effective with minimal inhibitory concentrations (MIC) in the range of 5 to 12.5% against both sensitive as well as multi-resistant aerobic bacteria. The exact mechanism of inhibitory action is unknown; possibly pentane-1,5-diol withdraws water from the bacterial cytoplasma, which makes the cell collapse. Importantly, it seems to be difficult for bacteria to develop resistance against pentane-1,5-diol. The high antimicrobial activity against multi-resistant bacteria has made pentane-1,5-diol an interesting agent for topical antimicrobial therapy in humans and animals.

The use of 2-methyl-pentane-2,4-diol in pharmaceutical compositions for transdermal delivery is disclosed in U.S. Pat. No. 4,855,294 A, U.S. Pat. No. 5,026,556 A, U.S. Pat. Nos. 5,041,439 A, 6,271,219 B1.

However, there is an increasing medical need to identify new antimicrobial compositions, which can be effectively used to inactivate microorganisms. In particular there is a growing list of microorganisms, such as bacteria, virus and fungi, which become resistant to antibiotics. Additionally, there is an increasing population of individuals becoming allergenic against a variety of antibiotics or preservative components used in antibiotic preparations, which also demands that novel compositions are developed which can be used as alternatives to conventional technologies.

SUMMARY OF THE INVENTION

The invention relates to a composition, such as a antimicrobial composition having improved properties such as being highly effective, non toxic, non allergenic, environmentally friendly and possible to manufacture at reasonable costs. By combining, specific different diols, it has surprisingly been found that it is possible to reduce/inhibit the growth of microorganisms to a higher extent compared to when the diols was used alone or combinations of similar diols.

The present invention relates to a composition comprising at least 3 different diols, wherein said diols have the general structure $(CH_2)_n H_2 O_2$, wherein n is the number of $CH_2$ and being between 3 to 10, in a total amount of from about 0.1 to about 50% (v/v), i.e., the first OH-group can be on the first carbon atom in all the diols and the second one at different carbon atoms, such as at carbon atom 2, 3, 4 or 5.

Additionally, the invention relates to a pharmaceutical composition comprising a pharmaceutically acceptable salt, diluent, excipient, carrier or adjuvant and the antimicrobial composition.

Additionally the invention relates to a cosmetic or a preservative composition.

Accordingly, the invention relates to the use of the composition, the pharmaceutical composition, the cosmetic composition, the antimicrobial composition or the preservative composition.

Additionally, the invention relates to a method of manufacturing a composition comprising the steps of; providing at least 3 different diols, adding a liquid or solid agent, mixing and obtaining a composition having a total amount of from about 0.1 to about 50% (v/v) of the diols.

Finally, the invention relates to a method of treating an antimicrobial infection comprising administering to a patient a therapeutically effective amount of a pharmaceutical composition as mentioned above.

By providing such a new composition, having such a broad use such as being an antimicrobial composition the list of compounds useful for inactivating microorganisms will be increased. Additionally, due to the unique properties (i.e., being able to inactivate more than one microorganism) the new invented antimicrobial composition will be suitable in cases were there is a need for inactivating more than one microorganism. Accordingly the invented compositions, shows an increased effect compared to other combinations of diols or when one and the same diol is used alone. It has also been found that by using the unique combination of diols as defined above it is possible to use a lower concentration of the different diols.

DETAILED DESCRIPTION OF THE INVENTION

In the context of the present invention the following definitions apply:

The term "inactivate" is intended to mean that the antimicrobial composition is capable of preventing and/or inhibiting and/or eliminating and/or reducing the amount of living microorganism.

The term "pharmaceutically active agent" is intended to mean any active agent, which could be used to treat a disorder or a disease. Examples are cortisone, antimicrobial agents, immuno modulating agents and acne agents.

Antimicrobial Composition

The present invention relates to a composition comprising at least 3 different diols, wherein said diols have the general structure $(CH_2)_nH_2O_2$, wherein n is the number of $CH_2$ and being between 3 to 10, in a total amount of from about 0.1 to about 50% (v/v), such as n being 3, 4, 5, 6, 7, 8, 9 or 10 or a mixture thereof. N may be different between the three different diols and at least one OH-group may be at different carbon atoms in the different diols or both at different carbon atoms. The composition may contain diols having different length. Furthermore, the diols may be selected from the group consisting of propane-1,2-diol, propane-1,3-diol, butane-1,2-diol, butane-1,3-diol, butane-1,4-diol, 2-methyl-propane-1,2-diol, 2-methylpropane-1,3-diol, pentane-1,2-diol, pentane-1,3-diol, pentane-1,4-diol, pentane-1,5-diol, pentane-2,3-diol, pentane-2,4-diol, 2-methyl-pentane-2,4-diol, hexane-1,2-diol, hexane-1,3-diol, hexane-1,4-diol, hexane-1,5-diol, hexane-1,6-diol, hexane-2,3-diol, hexane-2,4-diol, hexane-2,5-diol, hexane-3,4-diol, heptane-1,2-diol, heptane-1,3-diol, heptane-1,4-diol, heptane-1,5-diol, heptane-1,6-diol, heptane-1,7-diol, heptane-2,3-diol, heptane-2,4-diol, heptane-2,5-diol, heptane-2,6-diol, heptane-3,4-diol, heptane-3,5-diol, octane-1,2-diol, octane-1,3-diol, octane-1,4-diol, octane-1,5-diol, octane-1,6-diol, octane-1,7-diol, octane-1,8-diol, octane-2,3-diol, octane-2,4-diol, octane-2,5-diol, octane-2,6-diol, octane-2,7-diol, octane-3,4-diol, octane-3,5-diol, octane-3,6-diol and octane-4,5-diol such as a group consisting of diols having a length of from 3 to 6 carbon atoms, such from the group consisting of 2-methyl-pentane-2,4-diol, propane-1,2-diol, pentane-1,5-diol and butane-1,3-diol. One example being a mixture of 2-methyl-pentane-2,4-diol, propane-1,2-diol and pentane-1,5-diol.

The composition may contain at least 4 or 5 different diols.

The stereochemistry of the diols is not important to the present invention, and enantiomers, diastereomers, tautomers and racemic mixtures of diols may all be used with good results. Indeed, the requirement that the diols be "different" should be understood to mean that they differ in the connectivity of the atoms (regioisomerism) and not in whether they are e.g. R/S or +/−.

Additionally the composition may comprise at least 4 or 5 different diols. If the composition is used as an antimicrobial composition the number of the diols is depending on which microbe is to be inactivated. The diols may be present in an amount of from about 0.25-50% v/v, such as from about 0.25 to about 20% v/v. For example 0.25, 0.5, 1, 2, 3, 4, 5 6, 7, 8, 9, 10, 11, 12, 13, 14, 15, 16, 17, 18, 19 or 20% v/v.

The percentages given in this text should be understood as amounts calculated on a volume/volume basis.

Additionally, the composition may comprise at least one additional component such as an alcohol, for example ethanol.

Accordingly, the composition if it is to be used as an antimicrobial composition, comprises an additional agent or mixture of agents, such as one or more antimicrobial agents. Examples of such agents are fusidic acid, gentamycin, neomycin, allylamines, ciclopirox, amorolfine, nystatin, amphotericin, i.e., antibacterial, antiviral and antifungal agents, such as imidazoles, acyclovir, and vectavir.

The composition of the invention may take the form of a liquid, semi-liquid or solid disinfectant preparation, a bacteriostatic solution, lotion, cream, soap, shampoo, ointment, paste, wet towel, hygiene dish, patch, diaper or similar personal hygiene article. One form of the composition is a topical composition useful for all kind of topical administration, including dry skin repair, treatment of different disorders including microbial ones as well as applied to mucous membranes such as the membranes of the eye and the ear. The invention also relates to a pharmaceutical composition comprising the above-defined composition, including a pharmaceutically acceptable salt, diluent, excipient, carrier or adjuvant Pharmaceutical compositions of the invention are typically administered in a composition that includes one or more pharmaceutically acceptable adjuvants or excipients. Such pharmaceutical compositions may be prepared in a manner known in the art and are sufficiently storage-stable and suitable for administration to humans and animals.

"Pharmaceutically acceptable" means an adjuvant or excipient that—at the dosage and concentrations employed—does not cause any unwanted effects in the patients to whom it is administered. Such pharmaceutically acceptable carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000).

The pharmaceutical compositions may be subjected to conventional pharmaceutical operations such as sterilisation and/or may contain conventional adjuvants such as preservatives, stabilisers, wetting agents, emulsifiers, buffers, fillers, etc., such as disclosed herein.

The pharmaceutical composition according to the invention may be administered topically such as ointments, lotions, pastes, creams, gels, talc, sprays, solutions and emulsions. The ointments, lotions, creams and gels can contain, in addition to the antimicrobial agent or agents, excipients such as animal and vegetable fats, waxes, paraffins, starch, tragacanth, cellulose derivatives, polyethylene glycols, silicons, bentonites, silicic acid, talc and zinc oxide or mixtures of these substances. Talc and sprays can contain, in addition to the antimicrobial agent or agents, excipients such as lactose, talc, silica acid, aluminium hydroxide, calcium silicate and polyamide powders or mixtures thereof. Sprays may also contain propellants such as chloroflourohydrocarbons. Solutions and emulsions may contain excipients such as solvents, solubilising agents and emulsifiers such as water, ethyl alcohol, isopropylalcohol, ethylcarbonate, ethyl acetate, benzyl alcohol, benzyl benzoate, propylene alcohol, dimethylformamide, oils such as cottonseed oil, groundnut oil, corn germ oil, olive oil, castor oil and sesame oil, glycerol, glycerol formal, tetrahydrofurfuyl alcohol, polyethylene glycols and fatty acid esters such as sorbitan or mixtures thereof.

The pharmaceutical composition will be administered to a patient in a pharmaceutically effective dose. By "pharmaceutically effective dose" is meant a dose that is sufficient to produce the desired effects in relation to the condition for which it is administered. The exact dose is dependent on the, activity of the compound, manner of administration, nature and severity of the disorder, age and body weight of the patient, and different doses may be needed. The administration of the dose can be carried out both by single administration in the form of an individual dose unit or by several smaller dose units or by multiple administration of subdivided doses at specific intervals.

The pharmaceutical composition of the invention may be administered alone or in combination with other therapeutic agents. These agents may be incorporated as part of the same pharmaceutical composition.

The "patient" for the purposes of the present invention includes both humans and other mammal. Thus the methods are applicable to both human therapy and veterinary applications.

The invention also relates to a cosmetic composition or in topical formulations comprising the antimicrobial composition as defined above as a gel, cream, ointment, suspension, aerosol, paste, powder, lotion.

The invented composition, pharmaceutical composition, cosmetic composition, antimicrobial composition or preservative composition can be used to inactivate microorganisms selected from the group consisting of gram positive and gram negative bacteria, fungi, including yeasts, moulds and dermatophytes and virus. Examples include but are not limited to *Staphylococcus aureus*, Streptococci, gram negative rodes, *Candida albicans, Candida glabrata, Malassezia, M. furfur*, the mould Aspergillus flavus and the dermatophytes *Trichophyton rubrum, T. mentagrophytes, Epidermophyton floccusum, Microsporum canis*, papilloma virus, herpes virus and pox virus. Other useful uses are repair of dry skin.

The invention also relates to a method of manufacturing a composition as defined above comprising the steps of; providing at least 3 different diols as mentioned above, adding a liquid or solid agent, mixing and obtaining a composition, such as an antimicrobial composition having a total amount of from about 0.1 to about 50 (v/v) of the diols.

Accordingly, the invention relates to a method of treating an antimicrobial infection comprising administering to a patient a therapeutically effective amount of a pharmaceutical composition as defined above.

Finally, the invention relates to use of the above, mentioned diols as a preservative, without use of other preservatives such as parabenes, sodium lauryl sulphate, sorbic acid etc. A preservative may be used, for example, in contact lens solutions, shampoo, tooth paste, liquid soap, washing solutions, creams, ointments, pasta or cleaning solutions.

Following examples are intended to illustrate but not to limit the invention in any manner, shape, or form, either explicitly or implicitly.

Material and Methods.

Microorganisms.

*Staphylococcus aureus* number 515×6352 and *Candida albicans* H 29 were obtained from the Collection in the Department of Microbiology, Sahigrenska University Hospital, Gothenburg, Sweden. The isolates were maintained on blood agar at 37° C. *M. sympodialis* CBS 7222 and *M. globosa* CBS 7966

Compounds.

Propane-1,2-diol, pentane-1,5-diol and 2-methylpentane-2,4-diol and butan-1,3-diol were obtained from Merck Schuchardt, Hohenbrunn, Germany in a purity of 98 to 98.5%.

Example 1

Test for bacteriostatic effect (MIC=minimal inhitory concentration).

Each of the diols and their combination (1:1:1 volume/volume) was diluted directly with the test culture medium, Diagnostic Sensitivity test agar (DST) (Oxoid, UK) to obtain concentrations, in the test medium, of 2, 3, 4, 6, 9, and 12% volume percent of the respective diol and of 2, 3, and 4% of the respective diol in the combination.

*S. aureus* cells were added to the agar medium in concentrations of $10^3$ and $10^5$ cells/ml while *C. albicans* cells were added in a concentration of $10^6$ cells/ml and *M. sympodialis* and *M. globosa* in a concentration of $10^7$ cells/ml. Plates were incubated at 37° C. and analysed after 1 and 2 days. Each experiment was repeated. MIC (Minimum Inhibitory Concentration) was defined as the lowest concentration that totally inhibited growth. The MIC's for propane-1,2-diol, pentane-1,5-diol, 2-methylpentane-2,4-diol and the combination of these 3 diols are shown in the table 1.

The table shows the effect (MIC in %) of propane-1,2-diol, pentane-1,5-diol, 2-methylpentane-2,4-diol and their combination on the growth of *Staphylococcus aureus* and *Candida albicans* in vitro.

The combination of 3% of each of the 3 diols completely inhibited the growth of *S. aureus* and a combination of 2% completely inhibited the growth of *C. albicans* and a concentration of 0.5% completely inhibited the growth of *M. sympodialis* and *M. globosa*. With a combination of 4 diols a combination of 2% completely inhibited the growth of *S aureus* and a combination of 1% completely inhibited the growth of *C. albicans* and a concentration of 0.25% completely inhibited the growth of *M. sympodialis* and *M. globosa*. For *S. aureus*, the same activity was only obtained with a total of 12% pentane-1,5-diol and 2-methylpentane-2,4-diol when they were tested alone. Propane-1,2-diol, butane-1,3-diol and ethanol were not able to inhibit the growth of *S. aureus*, even at 12%.

TABLE 1

| Diol | S. aureaus $10^3$ | S. aureaus $10^5$ | C. albicans $10^6$ | M. sympodialis | M. globosa |
|---|---|---|---|---|---|
| Propane-1,2-diol | >12% | >12% | 9% | 10 | 10 |
| Butane-1,3-diol | >12% | >12% | 8% | 10 | 10 |
| Pentane-1,5-diol | 12% | 12% | 4% | 3 | 3 |
| 2-Methyl pentane-2,4-diol | 12% | 12% | 4% | 3 | 3 |
| Propane-1,2-diol + pentane-1,5-diol + 2-methyl pentane-2,4-diol in equal amounts | 3% | 3% | 2% | 0.5 | 0.5 |
| Ethanol | >12% | >12% | 8% | 10 | 10 |
| Propane-1,2-diol + butane-1,3-diol + pentane-1,5-diol + 2-methyl pentane-2,4-diol in equal amounts | 2% | 2% | 1% | 0.25 | 0.25 |

Example 2

Preparation of a Bacteriostatic Topical Pharmaceutical Composition

A mixture of equal amount of propane-1,2-diol+pentane-1,5-diol+2-methyl pentane-2,4-diol were mixed with the Essex® cream base (Schering Plough) to a final concentration of 2 or 3%.

Example 3

Example 3 was performed as example 1.

| Mixtures Final 3% | Effect against S aureus | Effect against C. Albicans |
|---|---|---|
| butane-1.3-diol, pentane-1,5-diol heptan-1.2-diol | + | + |
| propan-1,2-diol pentane-1,5-diol heptan-1.3-diol | + | + |
| pentane-1,5-diol 2-methyl pentane-2,4 diol hexan-1.2-diol | + | + |
| butan-1.4-diol pentane-1,5-diol 2-methyl pentane-2,4 diol | + | + |
| butan-1.3diol propane-1,2-diol heptan-1.5-diol | + | + |
| etan-1.2 diol butan-1.2 diol propane-1.2 diol | − | − |

+ indicates that the composition shows an effect
− indicates that the composition show less effect or no effect

The invention claimed is:

1. An antimicrobial composition for reducing growth of microorganisms, the antimicrobial composition consisting of active antimicrobial diols and pharmaceutically acceptable salts, diluents, excipients, carriers, or adjuvants, wherein the active antimicrobial diols are selected from 2-methyl-pentane-2,4-diol, propane-1,2-diol, pentane-1,5-diol, and butane-1,3-diol, wherein the composition include at least 3 different diols, and wherein the diols are present at 0.25 to 5% (v/v) of the total composition, and wherein the antimicrobial composition is able to reduce the growth of microorganisms to a higher degree than the diols used alone.

2. The composition according to claim 1, wherein the diols consist of 2-methyl-pentane-2,4-diol, propane-1,2-diol and pentane-1,5-diol.

3. The composition according to claim 1, wherein the diols are present in an amount from 0.25 to 4% (v/v).

4. The composition according to claim 2, wherein the diols are present in an amount from 0.25 to 4% (v/v).

5. The composition according to claim 1, wherein the diols are present in an amount from 0.25 to 3% (v/v).

6. The composition according to claim 2, wherein the diols are present in an amount from 0.25 to 3% (v/v).

7. The composition according to claim 1, wherein the diols are present in an amount of 0.5, 1, 2, 3, 4, or 5% (v/v).

8. The composition according to claim 2, wherein the diols are present in an amount of 0.5, 1, 2, 3, 4, or 5% (v/v).

9. The composition of claim 1, wherein the composition is formulated as a pharmaceutical composition, and wherein the composition further comprises a pharmaceutically acceptable salt, diluent, excipient, carrier or adjuvant.

10. The composition of claim 1, wherein the composition is formulated as a cosmetic composition.

11. The composition of claim 1, wherein the composition is formulated as a preservative composition.

12. A composition according to claim 1, wherein the composition is in an ointment, lotion, paste, cream, gel, talc, spray, solution, emulsion soap, shampoo, wet towel, hygiene dish, patch or diaper.

13. The composition of claim 1, wherein the butane-1,3-diol is present at 0.25 to 2% (v/v).

14. The composition of claim 1, wherein 2-methyl-pentane-2,4-diol, propane-1,2-diol, and pentane-1,5-diol are present at a concentration that results in a greater than additive antimicrobial effect.

* * * * *